United States Patent [19]
Janoff et al.

[11] Patent Number: 6,030,639
[45] Date of Patent: *Feb. 29, 2000

[54] TREATMENT USING PROSTOGLANDIN AND PARTICULATE FORMULATIONS

[75] Inventors: Andrew S. Janoff, Yardley, Pa.; David F. Eierman, Kingston, N.J.

[73] Assignee: The Liposome Company, Inc., Princeton, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/652,259

[22] Filed: May 23, 1996

Related U.S. Application Data

[60] Division of application No. 08/371,541, Jan. 11, 1995, which is a continuation-in-part of application No. 08/179,739, Jan. 11, 1994, abandoned, which is a continuation-in-part of application No. 08/203,341, Jan. 11, 1994, abandoned.

[51] Int. Cl.[7] .......................... A61K 9/127; A61K 9/133; A61K 9/16
[52] U.S. Cl. .......................... 424/450; 424/489; 424/490; 424/497; 424/498; 514/573
[58] Field of Search .......................... 424/450, 489–502; 514/573

[56] References Cited

U.S. PATENT DOCUMENTS

| | | | |
|---|---|---|---|
| 4,411,894 | 10/1983 | Schrank | 424/199 |
| 4,493,847 | 1/1985 | Mizishuma et al. | 424/317 |
| 4,544,545 | 10/1985 | Ryan | 424/1.1 |
| 4,619,794 | 10/1986 | Hauser | 264/4.1 |
| 4,684,633 | 8/1987 | Imagawa et al. | 514/78 |
| 4,820,732 | 4/1989 | Shell et al. | 514/573 |
| 4,955,878 | 9/1990 | See et al. | 604/181 |
| 5,049,390 | 9/1991 | Wodjam | 424/450 |
| 5,079,005 | 1/1992 | Gupta | 424/408 |

FOREIGN PATENT DOCUMENTS

| | | |
|---|---|---|
| 0298280 | 1/1989 | European Pat. Off. . |
| 2050287 | 1/1981 | United Kingdom . |
| 93/02681 | 2/1993 | WIPO .......... A61K 31/557 |

OTHER PUBLICATIONS

Mizushima (1986) Drugs Exptl. Clin. Res. X 11(8) 681.
Mizushima (1987) J. Rheumatology 14, 97.
Hoshi, et al., "Prostaglandin E, incorporated in lipid microspheres in the treatment of peripheral vascular diseases and diabetic neuropathy", Drugs Exptl. Clin. Res. 12(8):681, 1986.
Mizishuma, et al., "A multicenter double blind controlled study of lipo–pgge1, gpe1 incorporated in lipid microspheres, in peripheral vascular discease secondary to connective tissue disorders", J. rheymatol. 14:97 (1987).

*Primary Examiner*—Collamudi S. Kishore
*Attorney, Agent, or Firm*—Rosanne Goodman

[57] ABSTRACT

Provided herein is a method of administering a free arachidonic acid metabolite to an animal, the method involving administration of the free metabolite and an endocytosable particle. This method can be used to treat animals afflicted with disorders characterized by cell activation and adhesion, inflammation or toxemia. Also provided is a method of treating a animal for such disorders by administration to the animals of a composition containing an anti-disorder effective amount of an endocytosable particle.

10 Claims, 14 Drawing Sheets

TREATMENT USING PROSTOGLANDIN AND PARTICULATE FORMULATIONS

This application is a division of U.S. Ser. No. 08/371,541, filed Jan. 11, 1995, pending which is a continuation-in-part of U.S. Ser. Nos. 08/203,341 and 08/179,739, filed Jan. 11, 1994.

Arachidonic acid, and other twenty carbon "essential" fatty acids having at least three double bonds, can be used to make prostaglandins (for a review, see, e.g., *Goodman and Gilman's The Pharmacological Basis of Therapeutics* (A. Goodman Gilman et al., eds.), Pergamon Press, New York (1990), pp. 600–611); L. Stryer, *Biochemistry* (2nd edition), W. H. Freeman and Co., New York (1981), pp. 853–854)). The various prostaglandins are grouped into several categories (A–I), which are distinguished by varying substituents on the five-carbon ring introduced into the twenty-carbon fatty acid precursor during prostaglandin synthesis. These groups can be further subdivided based upon the number, and position, of double bonds in the prostaglandins' carbon chains.

The prostaglandins can have a broad spectrum of biological activities. E series prostaglandins, for example, can affect smooth vascular muscle, e.g., arterioles, precapillaries, sphincters and postcapillary venules, and can be potent vasodilators. $PGD_2$, $PGF_{alpha}$ and $PGI_2$ can also have vasodilative effects. Prostaglandins, and related derivatives, can affect the functioning of blood cells, particularly neutrophils and platelets. $PGI_2$, for example, can inhibit platelet aggregation at concentrations as low as 1 nM (see *Goodman Gilman's The Pharmacological Basis of Therapeutics*, supra). Uterine contractions can be affected by PGE, PGF and PGI action. Prostaglandins can also affect renal, central nervous system and afferent nerve function. Various endocrine tissues typically respond to prostaglandins. Furthermore, prostaglandins can modulate inflammatory responses and can ameliorate toxemic disorders. Prostaglandins are believed to act on their target cells by way of cellular surface receptors; these receptors are believed to be coupled to second messenger systems by which prostaglandin action is mediated.

Mizishuma et al. (J. Rheumatol. 14:97 (1987)) and Hoshi et al. (Drugs. Exptl. Clin. Res. 12(8):681 (1986)) describe lipid microspheres containing prostaglandin $E_1$ ($PGE_1$). However, as disclosed in Mizishuma et al. (U.S. Pat. No. 4,493,847) and Imagawa et al. (U.S. Pat. No. 4,684,633), these "microspheres" are actually prostaglandin-containing fat emulsions. The emulsions are not particles, and do not offer the same therapeutic advantages as the compositions comprising a particle and an arachidonic acid metabolite provided herein. These references do not disclose any pharmaceutical or therapeutic activity for the emulsions themselves. Shell and See (U.S. Pat. Nos. 4,820,732 and 4,955,878) disclose treatments for reducing dysfunction during angioplasty procedures which involve administering prostaglandin-containing compositions to patients. These compositions also contain a carrier. However, the liquid carriers disclosed, e.g., dehydrated alcohols and saline solutions, in these patents do not comprise particles. The fat-laden microsphere carriers disclosed are taught to be at least as large as a red blood cell, i.e, at least 7 microns in diameter, and can be much larger. Administration of microspheres of such large size to animals can cause difficulties because the microspheres can become stuck in, and clog, small blood vessels e.g., lung capillaries. The particles disclosed in the Shell and See patents are larger than the particles used herein; the particles employed in the present invention, by contrast, can be safely administered to animals.

SUMMARY OF THE INVENTION

This invention provides a method of administering to an animal a free arachidonic acid metabolite, the method comprising administering to the animal a composition comprising a pharmaceutically acceptable carrier, the free metabolite and an endocytosable particle. Preferably, the composition is administered to a human. Preferably, the metabolite is a prostaglandin, more preferably a prostaglandin of the E series or of the I series, and still more preferably, prostaglandin E1. The particle, which can be any endocytosable particle, for example, a liposome, latex microsphere, polystyrene, xymozin, starch or gelatin particle; is preferably a liposome.

The method can be used therapeutically to administer free arachidonic acid metabolites to animals afflicted with disorders characterized by cell activation and adhesion, inflammation or toxemia including, without limitation, vaso-occlusive, toxemic, athritic and auto-immune disorders such as: reperfusion injury, post-traumatic shock, restenosis, myocardial infarction, vasculitis, acute respiratory distress syndrome, systemic inflammatory response syndrome, rheumatoid arthrits, gout, systemic lupus erythematosus, juvenile dianetes, multiple sclerosis and Hashimoto's thyroiditis. Particularly preferred therapeutic indications are acute respiratory distress syndrome and systemic inflammatory response syndrome. The disorder treated can be a disorder that is exacerbated by exposure of the animal to a free arachidonic acid metabolite in the absence of an endocytosable particle.

Accordingly, an amount of the composition comprising an anti-disorder effective amount of the metabolite and particle is administered to the animal. Typically, the anti-disorder effective amount of the composition comprises from about $10^{-12}$ g of the metabolite per kg of body weight of the animal to about $10^{-3}$ g per kg; desirably the anti-disorder effective amount comprises from about $10^{-8}$ g to about $10^{-4}$ g, and more desirably, about $10^{-6}$ g of the metabolite per kg.

Preferably, but not necessarily, the endocytosable particle is about spherical in shape. More preferably, the particle is a spherical particle having a diameter of from about 50 nm to about 1000 nm. Typically, the anti-disorder effective amount of the composition comprises from about $10^{10}$ of such endocytosable particles per kg of body weight of the animal to about $10^{14}$ of such particles per kg, or about $10^{-6}$ g of such particles per kg. Preferably, the anti-disorder effective amount of the composition comprises about $10^{-6}$ g of the metabolite plus the particle per kg of body weight of the animal, or about $10^{-6}$ g of the metabolite and from about $10^{10}$ to about $10^{14}$ of the particles per kg.

Also provided herein is a pharmaceutical composition comprising per dose a pharmaceutically acceptable carrier and an anti-disorder effective amount of a free arachidonic acid metabolite and an endocytosable particle.

Further provided is a method of treating an animal afflicted with a disorder characterized by cell activation and adhesion, inflammation or toxemia; the method comprises administering to the animal a composition comprising a pharmaceutically acceptable carrier and an anti-disorder effective amount of an endocytosable particle, for example, a liposome, latex microsphere, polystyrene, xymozin, starch or gelatin particle, is preferably a liposome. Preferably, the anti-disorder effective amount comprises from about $10^{10}$ to about $10^{14}$ endocytosable particles, or about $10^{-6}$ g of endocytosable particles, per kg of body weight of the animal. Preferred therapeutic indications are acute respiratory distress syndrome and systemic inflammatory response syndrome.

DETAILED DESCRIPTION

Figure 1:
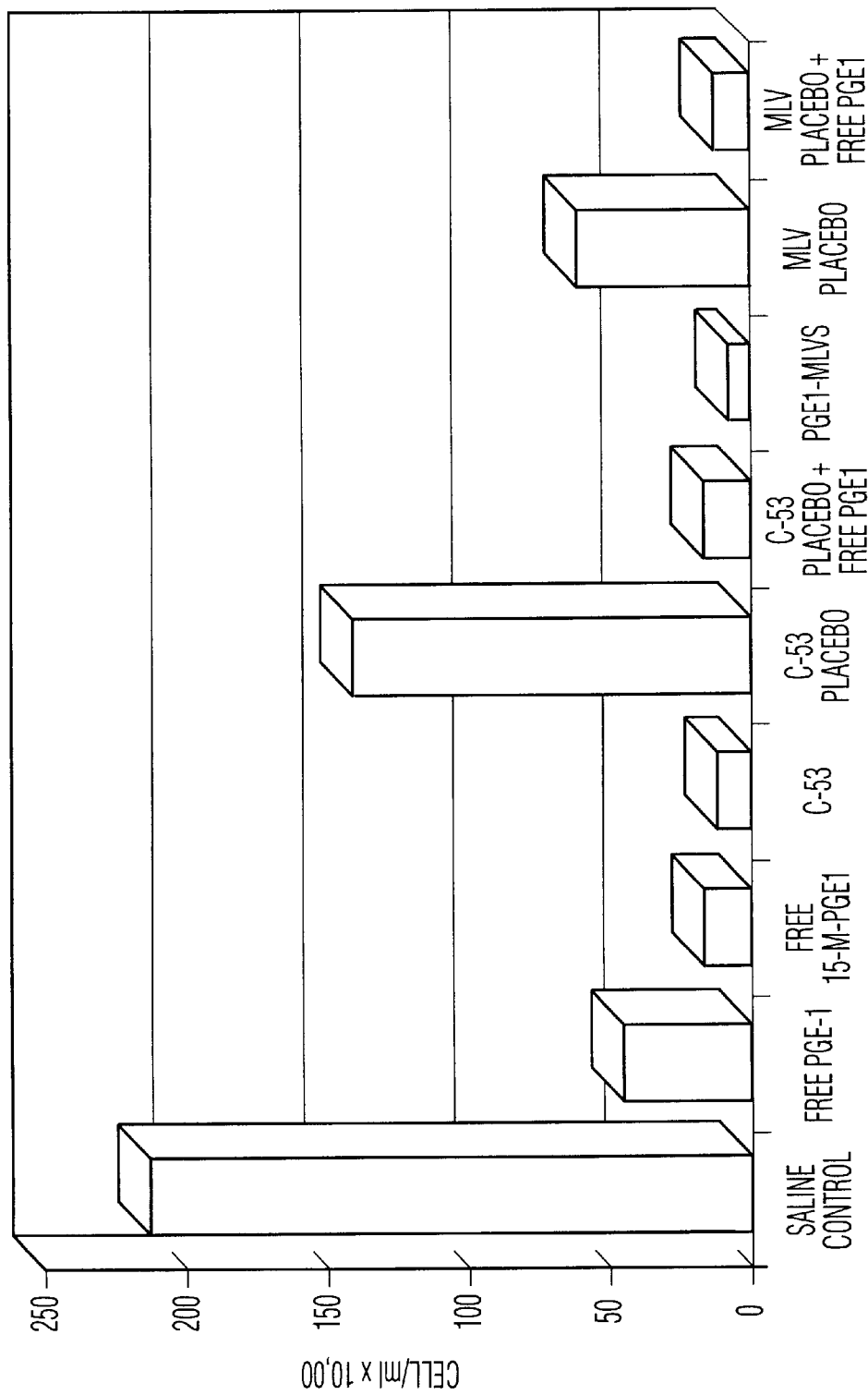
FIG. 1. Rat Air Pouch Studies. X-axis: saline control, free $PGE_1$, free 15-M-$PGE_1$ (15-methyl-$PGE_1$), LUV-$PGE_1$ formulation ("C-53"; unilamellar liposomal $PGE_1$, prepared in accordance with the procedures described in Example 1, below), LUV placebo liposomes ("C-53 placebo"; liposomes prepared in accordance with the procedures used to prepare LUV-$PGE_1$, but not having $PGE_1$), LUV placebo liposomes plus free $PGE_1$, MLV-$PGE_1$ (multilamellar liposomes, prepared in accordance with the procedures described in Example 1, below), MLV placebo liposomes (liposomes prepared in accordance with the procedures used to prepare MLV-$PGE_1$, but not having $PGE_1$), MLV placebo liposomes plus free $PGE_1$; y-axis: cells/ml times 10,000 in exudate.
Figure 2:
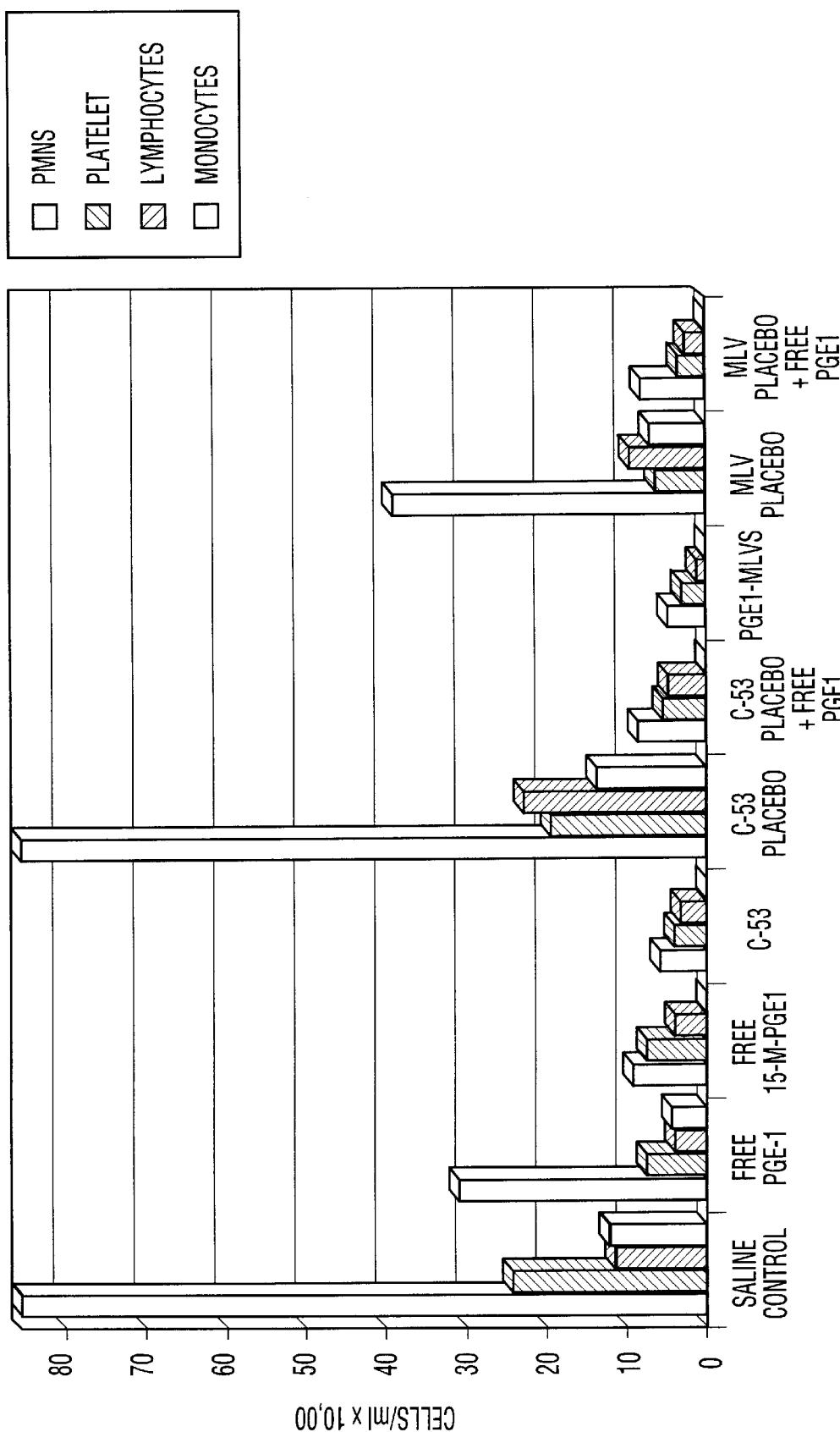
FIG. 2. Inhibition of Leukocyte Subset Extravasation. The graph is scaled for prostaglandins. The value for neutrophils in the saline control was off the scale used, and was $1.62 \times 10^6$ neutrophils/ml. First column in each set (unshaded): polymorphonucleocytes (PMNS); second column (lightly shaded): platelets; third column (darkly shaded): lymphocytes; fourth column (unshaded): monocytes. Y-axis: cells/ml×10,000 in exudate.
Figure 3:
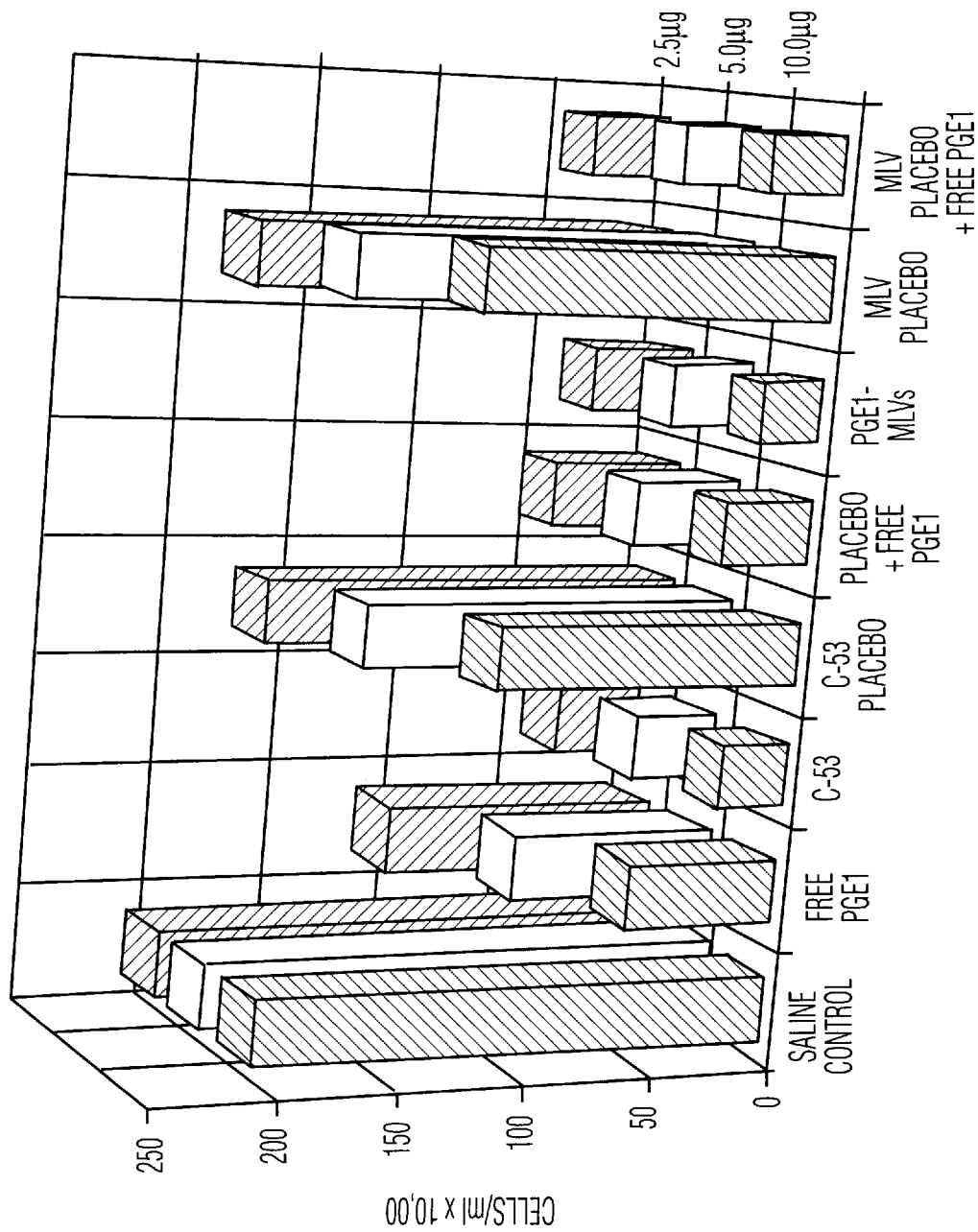
FIG. 3. Dose Response of Inhibition of Leukocyte Extravasation. The graph is scaled for prostaglandins. The value for neutrophils in the saline control was off the scale used, and was $1.62 \times 10^6$ neutrophils/ml. X-axis: saline control, free $PGE_1$, LUV-$PGE_1$, LUV placebo liposomes, LUV placebo liposomes plus free $PGE_1$, MLV-$PGE_1$, MLV placebo liposomes, MLV placebo liposomes plus free $PGE_1$; y-axis: cells/ml×10,000 in exudate. Darkly shaded columns: 25 g/kg $PGE_1$ or equivalent amount of placebo liposomes; unshaded: 50 g/kg; lightly shaded: 10 g/kg.
Figure 4:
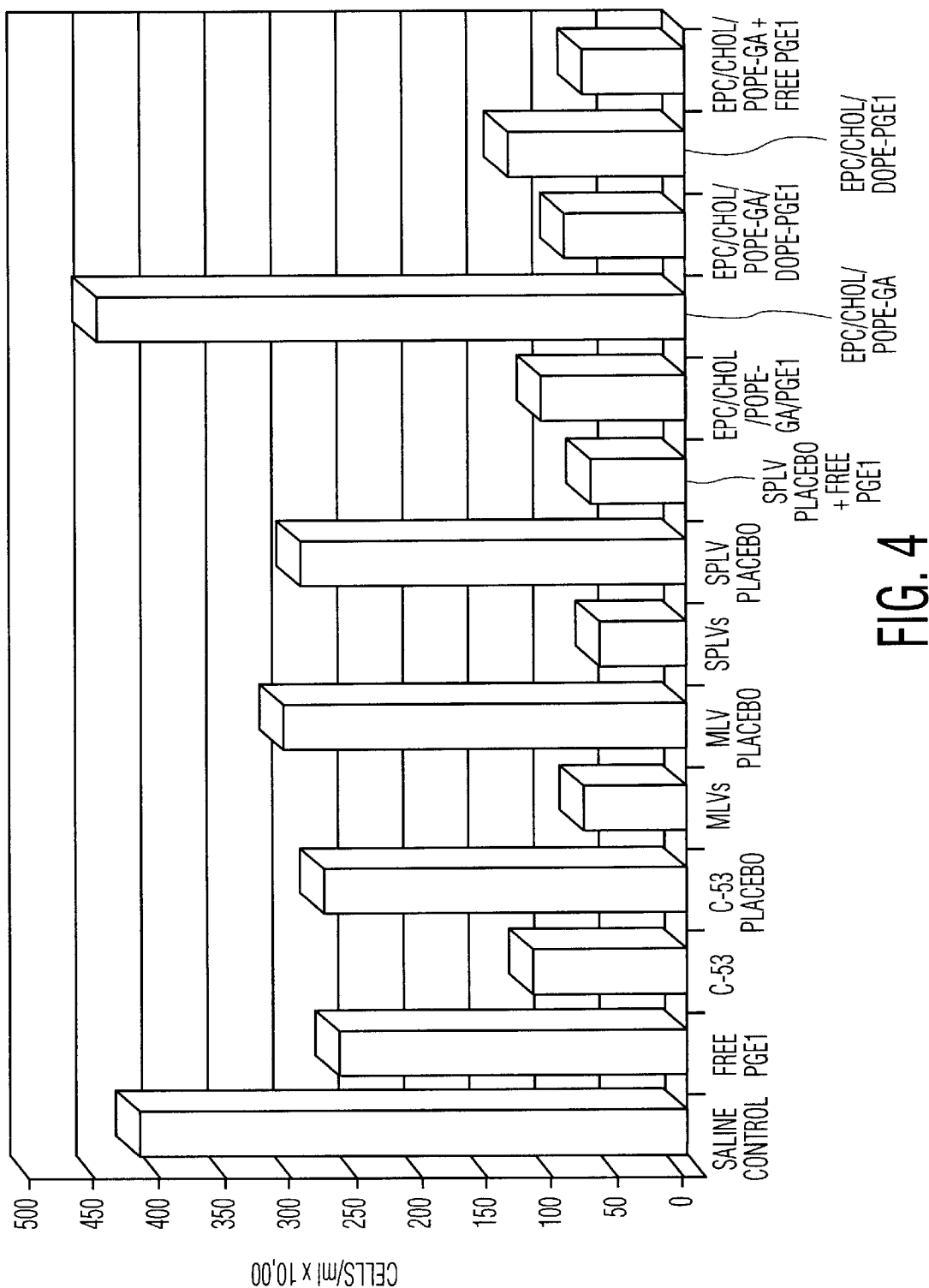
FIG. 4. Inhibition of Extravasation by Alternative Liposomal Formulations. X-axis: saline control, free $PGE_1$, LUV-$PGE_1$, LUV placebo liposomes, MLV-$PGE_1$, MLV placebo liposomes, SPLV-$PGE_1$ (stable plurilamellar vesicle, see Lenk et al., U.S. Pat. Nos. 4,522,803, 5,030,453 and 5,169,637), SPLV placebo liposomes, SPLV placebo plus free $PGE_1$, EPC/Cholesterol (Chol)/POPE-GA (1-palmitoyl-2-oleoyl-phosphatidylcholine-glutaric acid)-$PGE_1$, EPC/Chol/POPE-GA (no $PGE_1$), EPC/Chol/POPE-GA/DOPE-$PGE_1$ (dioleoyl phosphatidylethanolamine covalently linked to $PGE_1$), EPC/Chol/DOPE-$PGE_1$, EPC/Chol/POPE-GA placebo plus free $PGE_1$; y-axis: cells/ml× 10,000.

This invention provides a method of administering a free arachidonic acid metabolite to an animal, which comprises administering to the animal a composition comprising a pharmaceutically acceptable carrier, the free metabolite and an endocytosable particle. Preferably, the animal is a human.

"Pharmaceutically acceptable carriers" are any of the standard carriers, diluents, excipients and the like generally intended for use in connection with the administration of biologically active agents to animals. Such carriers are well known in the art and are generally chosen with regards to a number of factors, such as the particular drug being used and the intended route of administration, well understood by the ordinarily skilled artisan, or within his purview to determine without undue experimentation. Suitable carriers include, but are not limited to salt solutions such as physiological saline, aqueous buffered solutions, and the like. The pharmaceutical composition can further comprise auxiliary agents such as preservatives, anti-oxidants and the like in amounts, and for reasons, well known to the ordinarily skilled artisan. The pharmaceutical composition can be provided as a unit dosage form.

"Arachidonic acid metabolites" are prostaglandins, or compounds which can be converted to prostaglandins, e.g., artificially or in the body of an animal. Prostaglandins are a group of twenty-carbon fatty acids containing a five-carbon ring, plus seven- and eight-carbon chains, that are made from arachidonic acid and other twenty-carbon fatty acids having at least three double bonds (e.g., the "essential" fatty acids 8,11,14-eicosatrienoic acid, 5,8,11,14-eicosatetraenoic acid or 5,8,11,14,17-eicosapentanoic acid; see, e.g., *Goodman and Gilman's The Pharmacological Basis of Therapeutics*, supra). Arachidonic acid is the most abundant of these twenty-carbon prostaglandin precursors in humans.

The twenty-carbon essential fatty acid prostaglandin precursors, intermediates formed during prostaglandin synthesis, e.g., prostanoic acid, and structural analogs which can be converted to these compounds, are "arachidonic acid metabolites." "Prostaglandin-related compounds," e.g., leukotrienes, thromboxanes, lipoxins and prostacyclins, include those compounds which are functionally related to prostaglandins and which can also be derived from the twenty carbon essential fatty acid prostaglandin precursors; prostaglandins and prostaglandin-related compounds are also "arachidonic acid metabolites."

Preferably, the arachidonic acid metabolite administered to animals in accordance with the practice of this invention is a prostaglandin, more preferably, an E or I series prostaglandin, and most preferably, prostaglandin E1. The prostaglandin can also be 15-methyl-$PGE_1$ or $PGD_2$.

The term "free", as used herein with respect to an arachidonic acid metabolite, describes the relationship between the metabolite and a particle coexisting in the same aqueous medium. The metabolite and particle are generally not found at a greater local concentration in the medium in connection with each other than the concentrations at which they will be found elsewhere in the medium. That is, the metabolite and particle are not preferntially associated with each other in the aqueous medium.

An endocytosable particle is a particle that can be endocytosed by endocytic cells typically found in animals. Endocytosis (see, e.g., J. E. Darnell et al., *Molecular Cell Biology*, Scientific American Books, Inc. (New York), 1987, pp. 638–644, the contents of which are incorporated herein by reference) is the process by which a region of a cell's plasma membrane binds to, and envelops, a particle in the external medium. As used herein, "endocytosis" includes phagocytosis, the process by which cells take in relatively large particles in the surrounding medium.

Macrophages and monocytes are typical phagocytic cells (phagocytes). Particles phagocytosed by such cells are generally first coated with serum antibodies on their external surfaces. Surface receptors on the phagocytes bind to a region common to the various antibodies present in an animal's serum. Such binding between proteins on particle surfaces and cellular receptors stimulates phagocytosis. The process generally proceeds with the sequential binding of phagocyte surface receptors to antibodies bound to the particle's external surface, until the particle is completely engulfed by the plasma membrane.

Accordingly, the endocytosable particles of this invention are particles having surfaces that can be coated with the serum proteins generally believed to be responsible for recognition of particles by animal endocytic cells. Endocytosable particles of this invention generally have sizes, and corresponding surface areas, effective for coating with a sufficient number of antibody molecules to allow for phagocytosis of the particle, but are generally not so large that they tend to accumulate in small blood vessels. Typically, the most desirable endocytosable particle is about spherical and has a size (diameter) of at most about 5000 nm. More desirably, the endocytosable particle has a size of from about 50 nm to about 1000 nm, and still more desirably, about 100 nm. Methods of determining particle size, e.g., by dynamic light scattering, are well known to those of ordinary skill in the art and can readily be practiced by them without undue experimentation.

The endocytosable particle can be any endocytosable, pharmaceutically acceptable particle which can be safely administered to animals, and which can be combined with an arachidonic acid metabolite such that the metabolite is free and is capable of being therapeutically effective when administered to animals. It can be solid, or it can have one or more internal non-solid, e.g., aqueous, compartments. Suitable endocytosable particles include, without limitation: liposomes, latex microspheres, pansorbin™, xymozin, starch, gelatin or polystyrene particles. Additional endocytosable particles can readily be identified by ordinarily skilled artisans given the teachings of this invention , e.g., by use in vitro in connection with a free arachidonic acid metabolite, or by administration to suitable animal models, such as those described herein.

Liposomes are preferred herein as endocytosable particles. These are self-assembling structures comprising one or more lipid bilayers, each of which encompasses an aqueous compartment. Liposomes with a single lipid bilayer are unilamellar. Preferably in the practice of this invention, the unilamellar liposome is a large unilamellar liposome (LUV), i.e., a unilamellar liposome with a diameter of greater than about 50 nm. Liposomes having more than one lipid bilayer are multilamellar liposomes (MLVs). MLVs used in the practice of this invention preferably comprise a solute entrapped in their aqueous compartments, wherein the concentration of the solute in each of the aqueous compartments is substantially equal; i.e., the MLVs have substantially equal interlamellar solute distribution. Liposomes administered in a suspension in connection with a free arachidonic acid metabolite, but not entrapping, or having associated with them, the free metabolite at a greater concentration than that at which the metabolite may be found elsewhere in the suspension are endocytosable particles and can be referred to as "placebo" liposomes.

Liposomes can be produced by a variety of processes known in the art. (for a review, see, e.g., Cullis et al., in: *Liposomes, From Biophysics to Theraleutics* (M. Ostro, ed.), Marcel Dekker (New York), 1987, pp. 39–72). Bangham's procedure (J. Mol. Biol. 13:238–252 (1965)) produces "ordinary" multilamellar liposomes (MLVs). "Ordinary" MLVs can have unequal solute distribution amongst their aqueous compartments and thereby, osmotic stress between compartments. Lenk et al. (U.S. Pat. Nos. 4,522,803, 5,030,453 and 5,169,637), Fountain et al. (U.S. Pat. No. 4,588,578) and Cullis et al. (U.S. Pat. No. 4,975,282) disclose methods for producing multilamellar liposomes having substantially equal interlamellar solute distribution. Having substantially equal interlamellar solute distribution means that there will be less osmotic stress amongst the aqueous compartments of these MLVs, which will therefore generally be more stable than ordinary MLVs. Unilamellar liposomes can be produced from MLVs by sonication (see Paphadjopoulos et al. (1968)) or extrusion (Cullis et al. (U.S. Pat. No. 5,008,050) and Loughrey et al. (U.S. Pat. No.

5,059,421)). The contents of these disclosures are incorporated herein by reference.

Liposomes and other endocytosable particles, can contain, or have associated with them, one or more biologically active agents, i.e., compounds which can be administered to animals and which may have biological or diagnostic activity therein, or on an animal's cells in vitro. Biologically active, or bioactive, agents include, but are not limited to: antiviral, antibacterial, antifungal, antiparasitic, antimetabolic, antiglaucomic, anti-inflammatory or antineoplastic compounds, sterols, carbohydrates, amino acids, peptides, proteins, immunoglobulins, immunomodulators, dyes, toxins, enzymes, hormones, neurotransmitters, glycoproteins, radiolabels, radiopaque compounds, fluorescent compounds, cell receptor proteins, cell receptor ligands, mydriatic compounds, bronchodilators, local anesthetics, growth promoting agents, regenerative agents and the like. Biologically active agents used in the practice of this invention include, but are not limited to, antimicrobial, anti-inflammatory and vasodilative agents.

The method of this invention can be used to treat animals afflicted with a disorder characterized by cell activation and adhesion, inflammation or toxemia which comprises administering to the animal an amount of the composition which comprises an anti-disorder effective amount of the free arachidonic acid metabolite and the endocytosable particle.

Cell activation/adhesion disorders are characterized by abnormal activation of cells in the blood; the activated cells can adhere to each other, or to activated cells in surrounding vascular endothelium. Such adhesions can lead to the blockage of small blood vessels, e.g., lung capillaries, consequent stoppage of blood flow, and subsequent damage to surrounding tissue. Cell activation/adhesion disorders are a significant problem in a wide variety of medical pathologies. Endothelial cells, for example vascular, plural, pericardial or abdominal endothelial cells, can be activated by cytokines, e.g., interleukin-1 (IL-1), tumor necrosis factor-alpha (TNF-alpha) or bacterial endotoxins. In like manner, blood cells, particularly neutrophils and platelets, can be activated by agents such as GM-CSF, bacterial endotoxins, bacterial chemoattractants, TNF-alpha and the C5a component of complement.

Activated cells have adhesion sites on their surfaces by which they can adhere to each other. Activated and adhered cells can form clumps, which can clog small blood vessels such as those found in the lungs and heart, and thereby reduce blood flow to surrounding tissue. The activated cells can also adhere to activated vascular endothelial cells; such adhesion can lead to subsequent degranulation of vascular endothelium, or to the release of mediators of cell damage such as superoxide anion ($O_2^-$) and proteolytic enzymes. Accordingly, cell activation/adhesion can lead to the circulatory problems seen in animals afflicted with vaso-occlusive disorders.

Amongst the cell activation/adhesion disorders to which the present invention is directed are reperfusion disorders, such as those related to the reperfusion of occluded blood vessels, or incidental to surgery in which blood flow is temporarily stopped (see, e.g., Seewaldt-Becker et al., "Effect of Anti-Adhesive Antibodies on Reperfusion Injury," (Springer et al., eds.) in: *Leukocyte Adhesion Molecules*, Springer-Verlag, New York (1990) pp. 138–148; and "Adhesion in Disease and Therapy," (Springer et al., eds.), in: *Leukocyte Adhesion Molecules*, Springer-Verlag, New York (1990), pp. 85–156). When there is a blockage in a blood vessel, surrounding endothelial cells, as well as downstream ischemic tissue, can be damaged. There can even be further damage to nearby endothelial cells when the occlusion is cleared. Such damaged cells can in turn induce activation in neutrophils and platelets after restoration of blood flow to the affected areas.

The same cells which become activated and subsequently undergo intracellular adhesion can have surface receptors for arachidonic acid metabolites. Without intending to be limited by theory, it is believed that treatment with arachidonic acid metabolites, by binding to these receptors, can reduce cell activation/adhesion disorder-associated damage by deactivating the cell surface receptors responsible for the elevated levels of intercellular adhesion.

Inflammation is a process of cytological and histological reactions occurring in affected blood vessels, and surrounding tissues, in response to an injury or abnormal physical, chemical or biological stimulation (see, e.g., *Stedman's Medical Dictionary (Illustrated)* (24th edition, J. V. Basmajian et al., eds.), Williams and Wilkins, Baltimore, Md. (1982), pp. 707–708). Inflammatory responses include local reactions and resulting morphological changes, destruction or removal of injurious materials and activation of repair mechanisms. Agents, including arachidonic acid metabolites, that can inhibit inflammatory responses to injuries or abnormal physiological stimuli can be used to treat inflammatory disorders, e.g., gout, and various arthritic conditions, including rheumatoid arthritis.

Humoral inflammatory responses can be characterized by the extravasation of cells to the location of the agent inducing the response, that is, exit of cells from the circulatory system to the site of attack. The exudate can be characterized by a relatively low number of large cells, or by a relatively large number of neutrophils, eosinophils, monocytes, lymphocytes and plasma cells. Arachidonic acid metabolites, e.g., prostaglandins, can inhibit extravasation; without intending to be limited by theory, it is believed that this is a means by which such agents can inhibit inflammatory responses.

The rat air pouch exudate model, a well-accepted model for studying inflammation (see Tate et al, Laboratory Investigation 59: 192 (1988), the contents of which are incorporated herein by reference, and the Examples below), can be used to study the ability of arachidonic acid metabolites to inhibit extravasation. Rats acclimated to their environments are anesthetized, and pouches are formed in their backs by subcutaneous injection of air therein. Inflammation is then induced in the pouch by injection therein of an inflammation-inducing amount of an inflammatory agent, for example, fMLP. Cells are then expected to enter the air pouch by extravasation from the surrounding vasculature. The ability of an anti-inflammatory agent to inhibit such extravasation can be examined, for example, by injecting such agents into the animals and then comparing the number of cells entering the air pouch in agent-treated vs. control/untreated animals.

For example, as described below, rats were acclimated, then anesthetized and injected subcutaneously with 20 cc of ambient air. Six days thereafter, inflammation was induced by direct injection of 2.15 micrograms of fMLP into the air pouch. Free prostaglandin E1, free PGE-1 plus placebo liposomes, free PGE1 plus latex microspheres, placebo liposomes alone and latex microspheres alone were then injected into the animals via the tail vein. Six hours post-inflammation induction, the total exudate fluid was recovered from the air pouch. fMLP administration induced a substantial number of leukocytes to invade the air pouches;

the data show that administration of free PGE-1 (2.5, 5 and 10 micrograms) plus endocytosable particles significantly (greater than 50%, and as much as about 80%), reduced extravasation (as measured by cell concentration in the air pouch fluid) in comparison to the level of reduction achieved by administration of PGE-1 alone. It should be noted that the same inflammatory stimulator and anti-inflammatory agent can be used in similar experiments, but in amounts varying within ranges, and according to reasons, well within the purview of ordinarily skilled artisans to determine and control, given the teachings of this invention. Other stimulators and agents can be substituted for those specifically described herein, by ordinarily skilled artisans given the teachings of this invention, and can be used within ranges of amounts well within the purview of such artisans to determine.

Inflammation and anti-inflammatory action can further be studied by a number of models directed to arthritis induction, and inhibition by anti-arthritic agents, well accepted in the art for such purposes, for example, the rat adjuvant arthritis model described below. Rats are administered an arthritis inducer, for example, Freund's adjuvant, by well accepted means, such as intra-dural injection at the base of the tail vein. Ordinarily skilled artisans are well able to determine the appropriate amount of arthritis inducer, for example 10 micrograms of Freund's adjuvant per kg of rat body weight, to use. As joint inflammation is typically characterized by joint tenderness, pain and swelling, inhibition of swelling can be another measure of the effectiveness of an anti-arthritic agent, for example free PGE-1 plus endocytosable particles, as can the increased general health and motility of the treated animals.

Toxemia is the clinical manifestations observed during the course of infections by infectious agents, e.g., microbes, which contain toxins and other substances poisonous to host animals and which release such toxins inside tha animals (see, e.g., *Stedman's Medical Dictionary (Illustrated)*, pages 1274–1275 and 1464). Such infections frequently result from physical or chemical trauma. Fever, hypotension, changes in leukocyte counts and diarrhea are frequent symptoms accompanying toxemia induced by gram negative bacterial infections. Such infections can lead to disseminated intravascular coagulation and irreversible shock.

Toxemia, and the ability of agents to inhibit toxemia, can be studied by a number of models accepted by the art for such studies, for example, the rat endotoxemia model described below. An $LD_{50}$, that is, a dose of the endotoxin, e.g., *E coli* lipopolysachharide (LPS), lethal to about 50% of the test group, is first established; subsequently, animals are administered about this dose of the endotoxin. Animals are then either not treated with an anti-toxemia agent (control animals), or with such an agent, for example PGE-1 (e.g., at a dose of 40 micrograms per kg of the animal's body weight) or PGE-1 plus endocytosable particles (at a cumulative dose equivalent to the 40 microgram per kg dose of free PGE-1 alone). The ability of the anti-toxemia agent to inhibit endotoxin-induced mortality is then determined. Furthermore, inhibition of interleukin-1, interleukin-6 and tumor necrosis factor alpha secretion, a marker of toxemic conditions, can also be assessed; increasingly effective anti-toxemia agents are expected to decrease the percentage, vs. of untreated control, of the inhibition of secretion of these proteins that is induced by the endotoxin.

Data derived from the representative examples described herein, and presented below, indicate that free PGE-1 plus endocytosable particles was significantly more effective than free PGE-1 alone in increasing the survial rate in endotoxin-treated animals, and was significantly more effective in decreasing the percentage of endotoxin-induced secretion inhibition. For example, the data presented below show that administration of free PGE-1 plus placebo liposomes, in comparison to administration of free PGE-1 alone, can lead to about a five-fold increase in the rate of survival in LPS-treated animals, and to about a 40% decrease in secretion inhibition.

An "anti-disorder effective" amount of a free arachidonic acid metabolite and a particle, is any amount of the metabolite plus the particle effective, prophylactically or therapeutically, to ameliorate, alleviate, inhibit, eliminate or prevent a disorder characterized by cell activation and adhesion, inflammation or toxemia. The amount of the free arachidonic acid metabolite is generally equivalent to known therapeutic amounts of free arachidonic acid metabolites alone, in conditions treatable with arachidonic acid metabolites. However, conditions ordinarily exacerbated by exposure to arachidonic acid metabolites, such as inflammatory conditions induced or aggravated by prostaglandins, can be treated by coadministration of the same metabolites with endocytosable particles. Accordingly, for such conditions, there is a therapeutically effective amount of a free arachidonic acid metaboliute, used in connection with an endocytosable particle, where there is generally no such amount for the metabolite used alone.

Amounts of free arachidonic acid metabolites included in anti-disorder effective amounts of compositions comprising the metabolites and endocytosable particles are typically dependent upon a number of factors well within the purview of the ordinarily skilled artisan to understand and control, given the teachings of this invention. These include, without limitation: the particular metabolite and endocytosable particle used; the particular disorder with which the subject is afflicted; and the age, size, weight and general condition of the subject treated, including other disorders with which the subject may be aflflicted. Typically the anti-disorder effective amount of the composition comprises at least about $10^{-12}$ g of the free arachidonic acid metabolite per kg of body weight of the animal treated with the composition.

As described above, a "free" metabolite is a metabolite generally not found in greater concentrations with endocytosable particles than elsewhere in the same aqueous medium. Accordingly, the amount of free metabolite described can include some metabolite which is randomly located in the medium in proximity with the particles, or which is randomly associated with the particle's surfaces. Desirably, the anti-disorder effective amount comprises from about $10^{-12}$ g of the metabolite per kg of body weight to about $10^{-3}$ g per kg; more desirably, the anti-disorder effective amount of the composition comprises from about $10^{-8}$ g of the metabolite per kg of body weight to about $10^{-4}$ g per kg. Most desirably, the anti-disorder effective amount of the composition comprises about $10^{-6}$ g of the metabolite per kg of body weight.

Anti-disorder effective amounts of free arachidonic acid metabolite/endocytosable particle-containing compositions typically comprise a number of endocytosable particles at least sufficient to enhance the therapeutic response of animals to arachidonic acid metabolites, for conditions responsive to such metabolites; or, a number of particles sufficient to elicit a therapeutic response when administered with arachidonic acid metabolites, in conditions exacerbated by exposure to such metabolites in the absence of endocytosable particles.

As described above, "endocytosable particles" typically have surfaces which become coated with serum proteins; it is generally believed that such coating enhances the recognition of the particles, and their uptake, by endocytic cells. Without intending to be limited by theory, it is also believed that such particle endocytosis can have a therapeutic effect alone, as well as in connection with stimulating beneficial arachidonic acid metabolite interaction with target cells. Accordingly, the amount of particles included in anti-disorder effective amounts of compositions used herein is typically an amount of particles having a surface area sufficient for coating with an amount of serum proteins effective to enhance endocytosis. As described above, the endocytosable particles preferred for use herein are typically about spherical, although variations in shape are acceptable; the sperical particles typically have diameters of from about 50 nm to about 1000 nm.

Ordinarily skilled artisans given the teachings of this invention can determine the number and weight of endocytosable particles to employ in order to formulate and anti-disorder effective amount of the composition. As discussed herein, an amount of endocytosable particles at least sufficient to elicit, or enhance, a therapeutic response, is used to formulate the composition. The weight of this amount of particles is generally within the range of about $10^{-8}$ to about $10^{-4}$ g per kg of the animal's body weight, and is usually about $10^{-6}$ g or less, but can be outside this range if necesary. Ordinarily skilled artisans given the teachings of this invention can, without undue experimentation, determine if a higher or lower weight of a particular endocytosable particle should be used. For examples, such artisans can use the rat air pouch, adjuvant arthritis and endotoxemia models described herein to assess the anti-disorder effectiveness of a particular weight of the endocytosable particle, either alone or in connection with an amount of a free arachidonic acid metabolite. The number of endocytosable particles in the amount selected varies according to a variety of factors, such as the effective weight of particles selected, as well as the size, shape and densiy of the particles. For the preferred endocytosable partiles herein, this number is typically from about $10^{10}$ to about $10^{14}$, and can be about $10^{12}$.

Preferably, the anti-disorder effective amount of the composition comprises about $10^{-6}$ g of the metabolite plus the particle per kg, that is $10^{-6}$ g is about their combined weight, or about $10^{-6}$ g of the metabolite per kg and from about $10^{10}$ endocytosable particles to about $10^{14}$ particles. For example, the data presented herein show that both 40 micrograms, or $40 \times 10^{-6}$ g, of an endocytosable particle alone, a liposome or a latex microsphere, or 40 micrograms combined of a free arachidonic acid metabolite and an endocytosable particle can be more therapeutically effective in the models described herein.

Anti-disorder effective amounts of compositions described herein can be used to treat animals afflicted with disorders characterized by cell activation and adhesion, inflammation or toxemia. Accordingly, such amounts include anti-cell activation and adhesion, inflammation or toxemia amounts of a free arachidonic acid metabolite and an endocytosable particle. An "anti-cell activation/adhesion effective amount" of a free arachidonic acid metabolite and an endocytosable particle is any amount effective to ameliorate, inhibit or prevent the activation of adhesion sites on cells in the blood, or in surrounding vascular tissue, and/or the adhesion of such activated cells to other cells in the blood or surrounding vascular tissue. The anti-cell activation/adhesion amount is generally effective to inhibit or lessen vascular occlusion resulting from such activation and intracellular adhesion. An "anti-inflammatory disorder effective amount" of a free arachidonic acid metabolite and an endocytosable particle is any amount effective to ameliorate, inhibit or prevent abnormal inflammatory responses or reactions in animals afflicted with conditions characterized by abnormal inflammation, i.e., inflammation which is in response to abnormal physiological stimuli or injury. Such amounts are effective, for example, to prevent extravasation of cells from the circulation of the animal to the site of the abnormal inflammation. An "anti-toxemic disorder effective amount" of the free arachidonic acid metabolite and the particle is any amount effective to ameliorate, inhibit or prevent abnormal inflammatory responses or reactions in animals afflicted with toxemic conditions, e.g. toxemic conditions resulting from microbial infection or physical or chemical trauma.

Disorders treatable according to the method of this invention include, without limitation, vaso-occlusive, arthritic, traumatic and auto-immune disorders, such as: reperfusion injury, restenosis, myocardial infarction, vasculitis, post-traumatic shock, acute respiratory distress syndrome, systemic inflammatory response syndrome, rheumatoid arthritis, gout, systemic lupus erythematosus, juvenile diabetes, multiple sclerosis or Hashimoto's thyroiditis. Particularly preferred therapeutic indications are systemic inflammatory response syndrome (SIRS) acute respiratory distress syndrome (ARDS).

Treatable disorders according to the method of this invention include those exacerbated by exposure of the animal to a free arachidonic acid metabolite. As used herein, a disorder "exacerbated" by a free arachidonic acid metabolite is a disorder the severity of whose signs, symptoms or effects is increased by administration of a free arachidonic acid metabolite, but which can be ameliorated, alleviated, eliminated, inhibited, or prevented, therapeutically or prophylactically, by administration of a free arachidonic acid metabolite in connection with an endocytosable particle.

Also provided herein is a composition comprising per dose a pharmaceutically acceptable carrier and an anti-disorder effective amount of a free arachidonic acid metabolite and an endocytosable particle.

Further provided is a method of treating an animal afflicted with a disorder characterized by cell activation and adhesion, inflammation or toxemia; the method comprises administering to the animal a composition comprising a pharmaceutically acceptable carrier and an anti-disorder effective amount of an endocytosable particle, for example, a liposome, latex microsphere, polystyrene, xymozin, starch or gelatin particle, is preferably a liposome. The anti-disorder effective amount of the endocytosable particle alone can be about the same as the anti-disorder effective amount of the free arachidonic acid metabolite plus the particle. The effective amount of the particle can also be greater or less than this amount, as necessary. Ordinarily skilled artisans given the techings of this invention can, for example using the models described herein, determine the appropriate amount of a particular endocytosable particle to use, and whether this amount is outside of the range described as preferred herein. Preferably, the anti-disorder effective amount comprises from about $10^{10}$ to about $10^{14}$, or about $10^{-6}$ g, of endocytosable particles, per kg of body weight of the animal. Preferred therapeutic indications are acute respiratory distress syndrome and systemic inflammatory response syndrome.

This invention is further described in the following Examples. However, those of ordinary skill in the art will readily understand that these examples are merely illustrative of the invention as defined in the claims which follow thereafter.

EXAMPLES

Example 1

Preparation

Placebo Liposomes
Multilamellar Liposomes (MLVs)

An egg phosphatidylcholine (EPC) stock solution (20 mg/ml in ethanol) was prepared as follows: 1 g of dried EPC was dissolved in 50 ml of absolute ethanol, with gentle swirling, in a 50-ml brown bottle with a Teflon-lined lid. The resulting solution was stored at minus 20 degrees Celsius. An aliquot of the EPC stock solution was added to a round-bottom flask, from which the ethanol was removed by rotoevaporation at 30 deg. C. for at least two hours. The dried EPC was resuspended in a citrate buffer (50 mM citrate, 150 mM NaCl, brought to pH 4.5 with 10 N NaOH) so as to form a suspension of MLVs. For the preparation of DPPC-containing MLVs, a DPPC stock solution was prepared as described above using 1.035 g of dipalmitoyl phosphatidylcholine (DPPC).

Unilamellar Liposomes (LUVs)

Egg phosphatidylcholine (200 mg) in hexane:ethanol (95:5) was rotary evaporated under reduced pressure in a water bath set at 37 degrees Celsius to a thin film on the sides of the flask. The film was resuspended in 200 l of ethanol, and the ethanolic solution was drawn into a 1.0 ml tuberculin syringe and injected through a 21-gauge needle, at a rate of about 2 drops per second, into 4.0 ml of a stirring solution at pH 7.0, comprising 10% weight by volume of aqueous dextrose and 0.01% weight by volume aqueous EDTA. The solution became cloudy upon the addition of the ethanol/lipid mixture; the solution was extruded 5 times through a 0.1 micron polycarbonate straight-path filter, followed by a second series of five extrusion through the same type of filter.

Prostaglandin E1 Solutions

A $PGE_1$ stock solution (1 mg/ml in ethanol) was prepared as follows: 20 mg of dried $PGE_1$ was transferred to a 20-ml vial, to which 20 ml of absolute ethanol was added. The $PGE_1$ was dissolved in the ethanol with gentle swirling; the resulting solution was stored at minus 20 degrees Celsius.

Placebo liposomes suspensions, or suspensions of an equivalent number of latex microspheres, were mixed with the requisite amount of the $PGE_1$ solution.

Prostaglandin E1 Liposomal Formulations

For multilamellar liposomal $PGE_1$ formulations, an aliquot of the EPC or DPPC stock solutions (9.5 ml) and an aliquot of the $PGE_1$ stock solution (0.5 ml) were combined in the round-bottom flask prior to removal of the ethanol. For unilamellar liposomal $PGE_1$ formulations, 1.0 mg of $PGE_1$ was added to the ethanol used to resuspend the dried lipid prior to ethanol injection.

Example 2

Rat Air Pouch Studies

The rat subcutaneous air pouch, a model for acute inflammation and leukocyte extravasation from the peripheral vasculature to sites of inflammation (Tate, et al., Laboratory Investigation 59:192 (1988), the contents of which are incorporated herein by reference), was used to study the effect of systemic $PGE_1$ liposomes, no-liposomal $PGE_1$, and particles, in mediating fMLP induced inflammation.

Male Sprague-Dawley rats, weighing 126–150 g each, were obtained from Charles River Laboratories. Upon receipt, the rats were acclimated in the animal facility for 2 days. Throughout the experiments, the rats were watered and fed ad libitum. For air pouch formation, the rats were anesthetized via inhalent, their backs shaved, and swabbed with ethyl alcohol. Twenty cc of ambient air was injected subcutaneously into the animal's back to form an air pouch, and the animal was returned to it's cage. The air pouches were monitored to determine integrity, and additional air was injected, if warranted. For each treatment and control group, the number of rats (n) in each was six. At six days following air pouch formation, intra-air pouch inflammation was induced by direct injection into the air pouch of 2.15 g fMLP. Free $PGE_1$, $PGE_1$-placebo liposome, $PGE_1$ -latex microspheres, placebo liposome and latex microsphere formulations, were simultaneously injected i.v. via the tail vein, and the animals returned to their cages. Six hours after fMLP stimulation, the rats were sacrificed by $CO_2$ inhalation, and the total exudate fluid was recovered from the air pouch via syringe. The results of these experiments are presented in FIGS. 1–4.

Visual examination of the post-stimulation air pouch lining indicated that fMLP effected a thickening of the lining and a large number of invasive leukocytes, as compared to control animals, in which saline alone was injected into the air pouch. Treatment with free $PGE_1$ resulted in a reduction in vascular reactivity and a concurrent reduction in the number of leukocytes invading the pouch lining. The neutrophil population evident in the lining was transient, i.e., the leukocytes were in the process of extravasation from the vasculature to the lumen/exudate fluid of the air pouch. Since the leukocytes were transiently crossing the air pouch lining, subsequent analysis was confined to those cells present in the aspirated exudate fluid. The free stable prostaglandin analog 15-methyl-$PGE_1$ was included in these experiments due to its longer bioavailability of $\geq 8$ hours, as compared to the <15min. bioavailability of free $PGE_1$.

Example 3

Adjuvant Arthritis

Male Lewis rats, weighing 126–150 g each, were obtained from Charles River Laboratories. Upon receipt, the rats were acclimated in the animal facility for 2 days. Throughout the experiments the rats were watered and fed ad libitum. Chronic bilateral arthritis was induced by the i.d. (intradural) injection of complete Freund's adjuvant at the base of the tail. Free $PGE_1$ was injected into one group of rats, at a dose of 10 g/kg, beginning at day 0, with the injections repeated every second day. Free $PGE_1$ was also injected into another group, at a dose of 10 g/kg, beginning at day 10, and repeated every second day. Also administered was an adjuvant control (no $PGE_1$) and a saline control (no adjuvant). For each treatment group, n=6.

The onset of arthritis was abrupt, occurring between days 10 and 14 in the Freund's-induced animals. The symptoms exhibited by untreated control animals were tenderness upon palpation in most active joints, symmetric edema involving the joints of the paws, ankles and knees, flexation contractures of the forepaws, malaise, and weight loss attributable to both primary disease as well as inability or disinclination to access food supplies, due to pain and decreased mobility.

Figure 5:
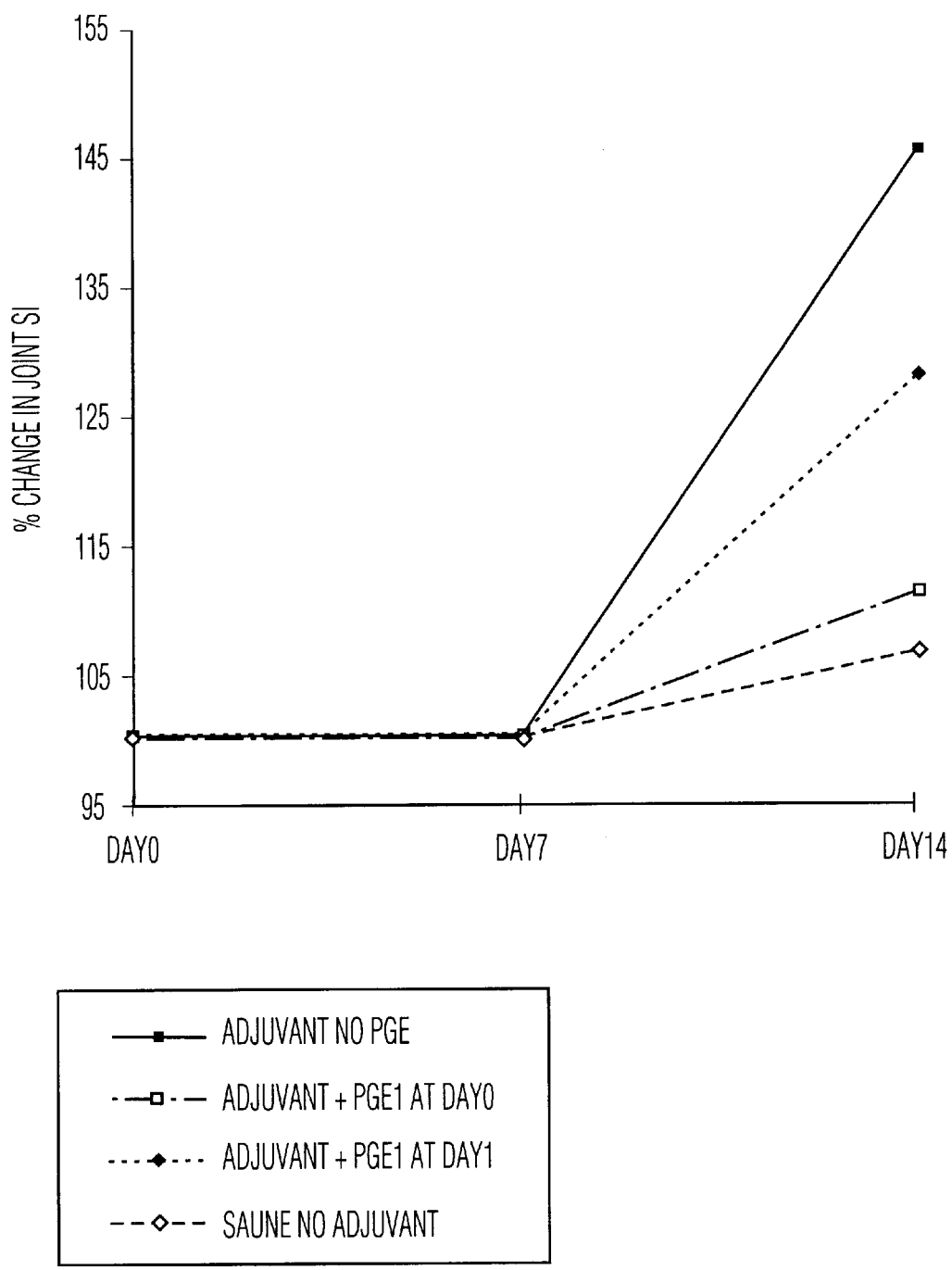
FIG. 5. Adjuvant Arthritis/Free $PGE_1$. X-axis: time (days); y-axis: % change in jaw size. Filled squares: adjuvant control (no $PGE_1$); open squares: adjuvant and $PGE_1$ administered at day 0; filled diamonds: adjuvant administered at day 0, $PGE_1$ at day 10; open diamonds: saline control (no adjuvant).
Figure 6:
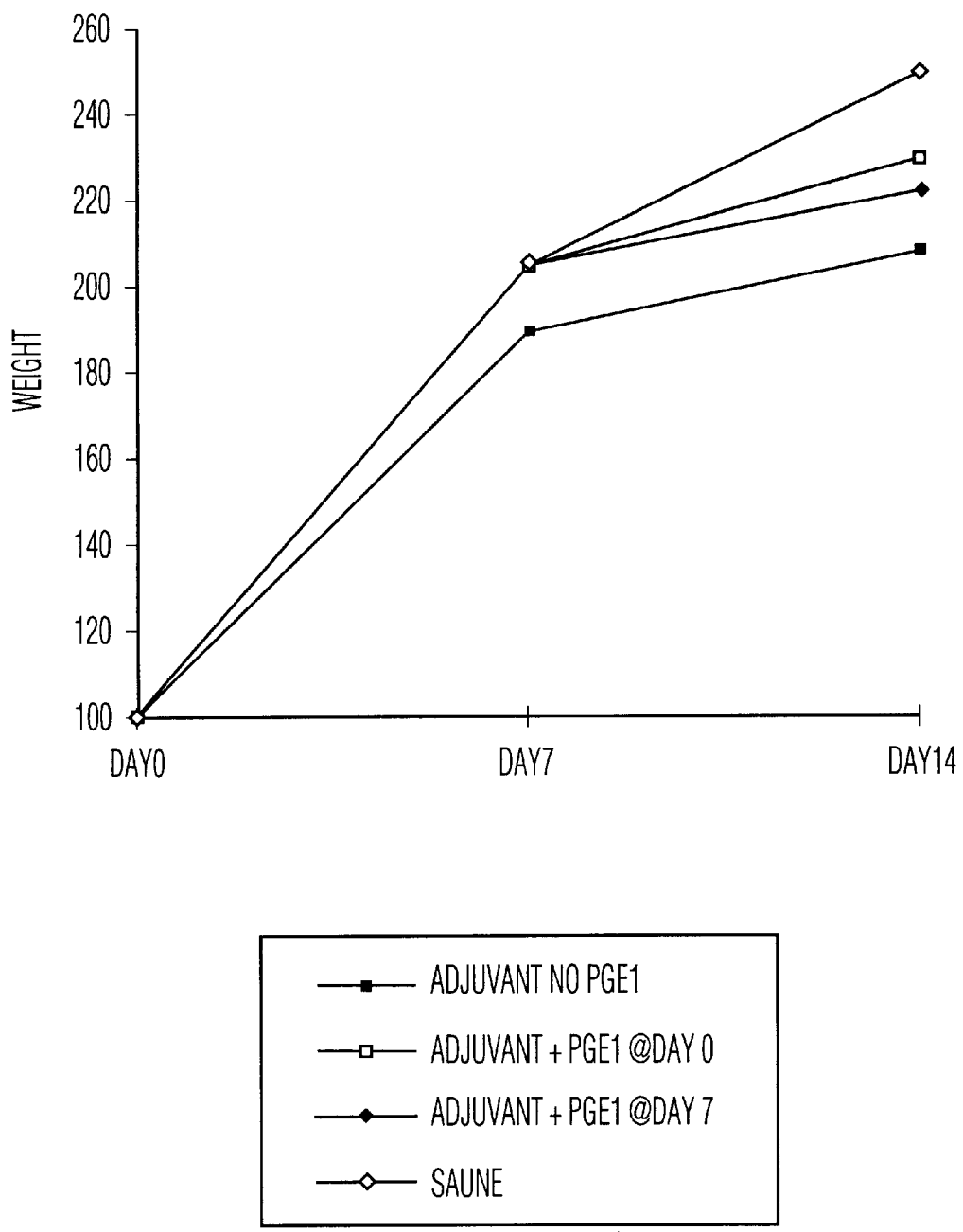
FIG. 6. Adjuvant Arthritis/Free $PGE_1$. X-axis: time (days) post-adjuvant administration; y-axis: percent weight change. Filled squares: adjuvant control; open squares: adjuvant plus $PGE_1$ at day 0; filled diamonds: adjuvant plus $PGE_1$ at day 10; open diamonds: saline control.
Figure 7:
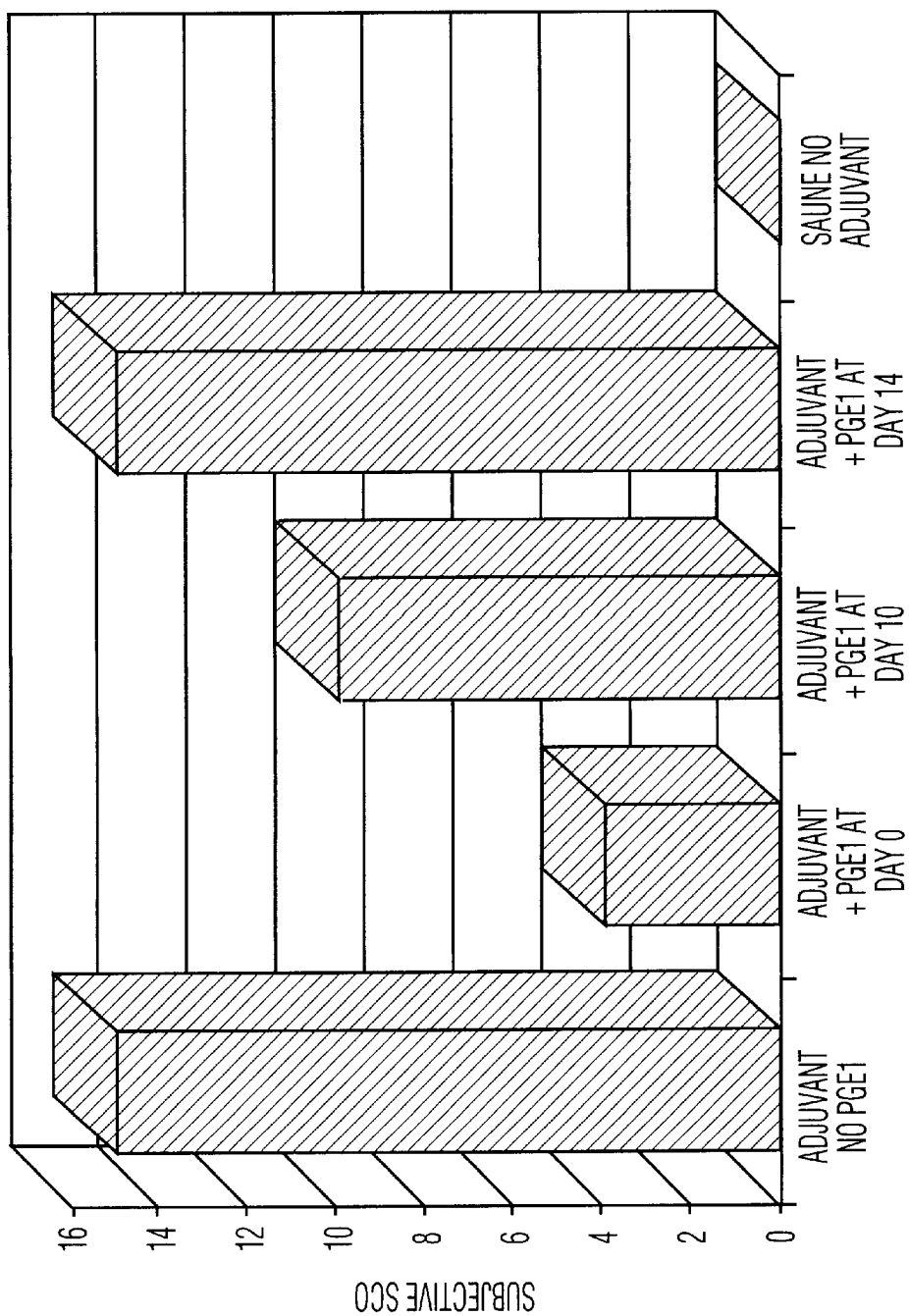
FIG. 7. Rat General Health/Motility. X-axis: adjuvant control, adjuvant plus $PGE_1$ at day 0, adjuvant plus $PGE_1$ at day 10, adjuvant plus $PGE_1$ at day 14, saline control (no adjuvant); y-axis: subjective score.

Experiments were conducted to assess the efficacy of free $PGE_1$, as well as prostaglandin E1 in connection with placebo liposomes and latex microspheres, placebo liposomes alone and latex microspheres alone, in mediating the progression of adjuvant arthritis. The parameters assessed in these experiments were changes in joint size measured at the rear knee, assessments of which were made on a weekly basis, changes in body weight, and a subjective scoring of general health, vigor and motility. The results from these experiments are shown in FIGS. 5–7.

Example 4

Rat Endotoxemia

Fever, hypotension, changes in leukocyte counts and diarrhea are symptoms of gram-negative bacterial infections. These infections may lead to disseminated intravascular coagulation and irreversible shock. A large volume of literature indicates the involvement of leukocyte derived IL-1, IL-6 and TNF in mediating the progression of endotoxic shock. Because our in vitro data indicated an inhibition of these cytokines from cultured monocytes, we developed an in vivo model of rat endotoxemia, using mortality as an end point, to assess the effectiveness of $PGE_1$ and particulate formulations in attenuating LPS-induced death.

Figure 8:
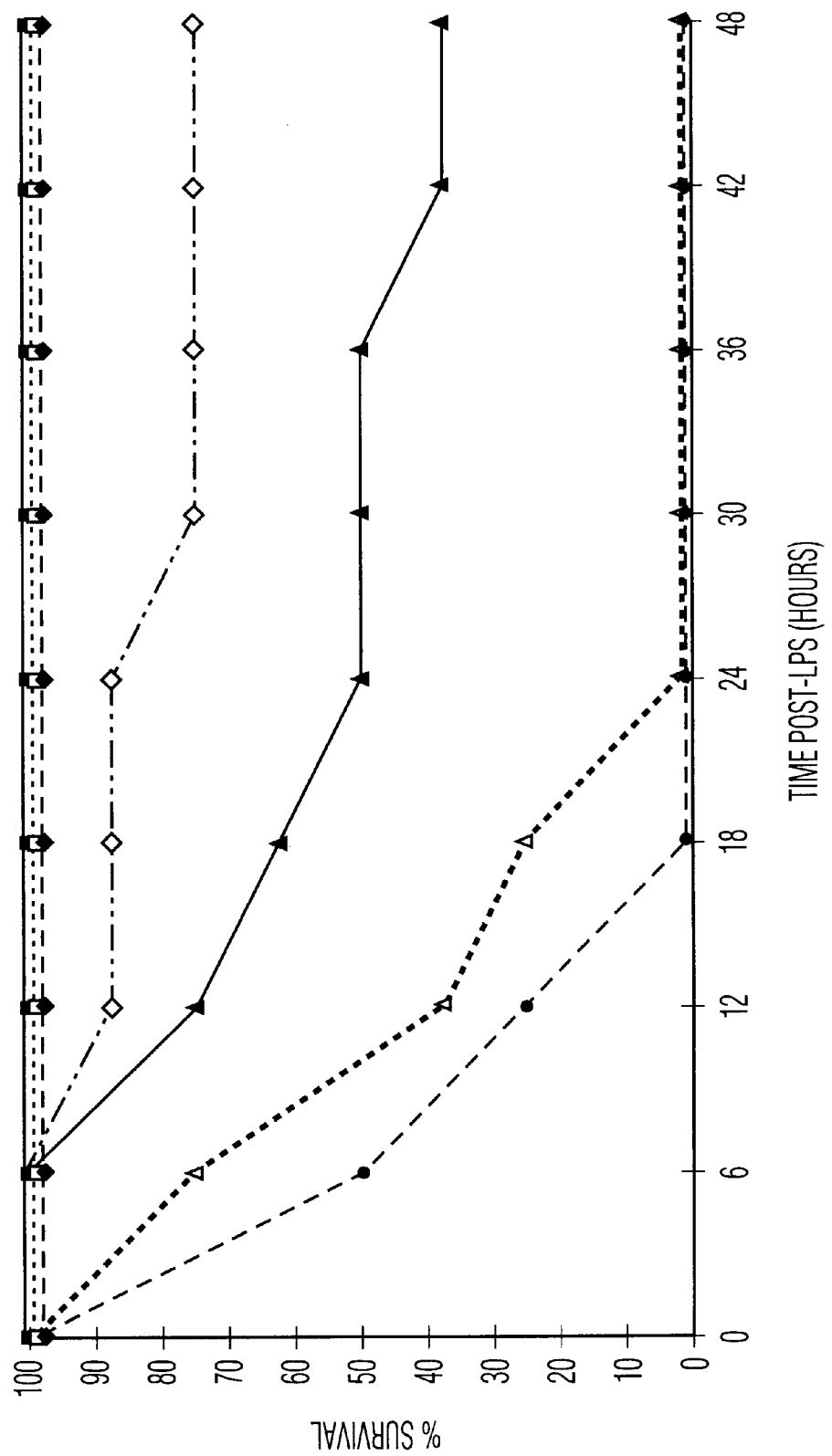
FIG. 8. Rat Endotoxemia Model. X-axis: time (days) post-LPS administration; y-axis: percent survival in treatment group. Filled squares: rats administered saline control (0 g/kg LPS); open squares: rats administered 10 g/kg LPS; filled diamonds: 15 g/kg LPS; open diamonds: 25 g/kg LPS; filled triangles: 50 g/kg LPS; open triangles: 75 g/kg LPS; filled circles: 100 g/kg LPS.

Experiments were designed to establish an $LD_{50}$ for *E. coli* LPS (lipopolysaccharide; serotype 055:B5) in Sprague-Dawley rats. The data from these experiments are shown in FIG. 8, and indicate that the $LD_{50}$ is at 50 g/kg. This LPS dosage was used in subsequent experiments, unless otherwise indicated.

Male Sprague-Dawley rats, weighing 126–150 g each, were acclimated for two days in an animal facility with food and water ad libitum. At time 0, groups of rats (n=16) were injected i.v. with either *E. coli* lipopolysaccharide as a single bolus, or with a saline (no LPS) control. Mortality was assessed at various times (days) post-LPS administration.

Example 5

Figure 9:
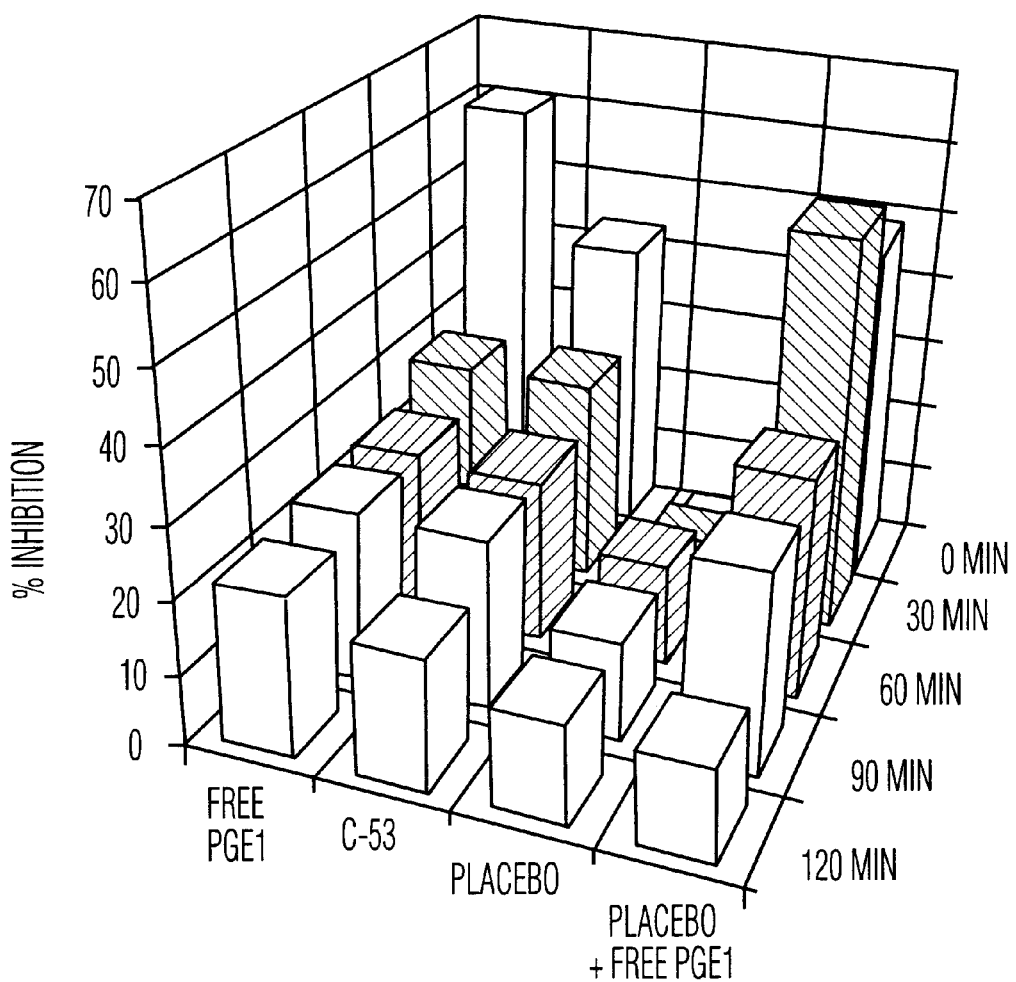
FIG. 9. Placebo Liposomes Inhibit Secretion of Human Monocyte TNF and II-1 in Response to Lipopolysaccharide (LPS). X-axis: free $PGE_1$, LUV-$PGE_1$, placebo LUVs, placebo LUVs and saline control (no liposomes or $PGE_1$); y-axis: percent inhibition of TNF and IL-1 secretion; unshaded: TNF; shaded: IL-1.

Inhibition of Tumor Necrosis Factor Alpha (TNF) and Interleukin-1 Beta (IL-1) Synthesis in Response to Lipopolysaccharide (LPS) and $PGE_1$ Adherent human monocytes were stimulated with LPS (1 g/ml/$10^6$ cells) at time 0. Free $PGE_1$ (not entrapped in liposomes), LUV-$PGE_1$ (large unilamellar liposomes (LUVs) plus free $PGE_1$), LUV-$PGE_1$ "placebo" liposomes (LUVs not containing $PGE_1$) plus free $PGE_1$, placebo liposomes or a saline control (no $PGE_1$) were injected simultaneously (10 M $PGE_1$). Secreted TNF and IL-1 were assayed at three hours. Results from these experiments are presented in FIG. 9.

Example 6

Rat Endotoxemia Model

Figure 10:
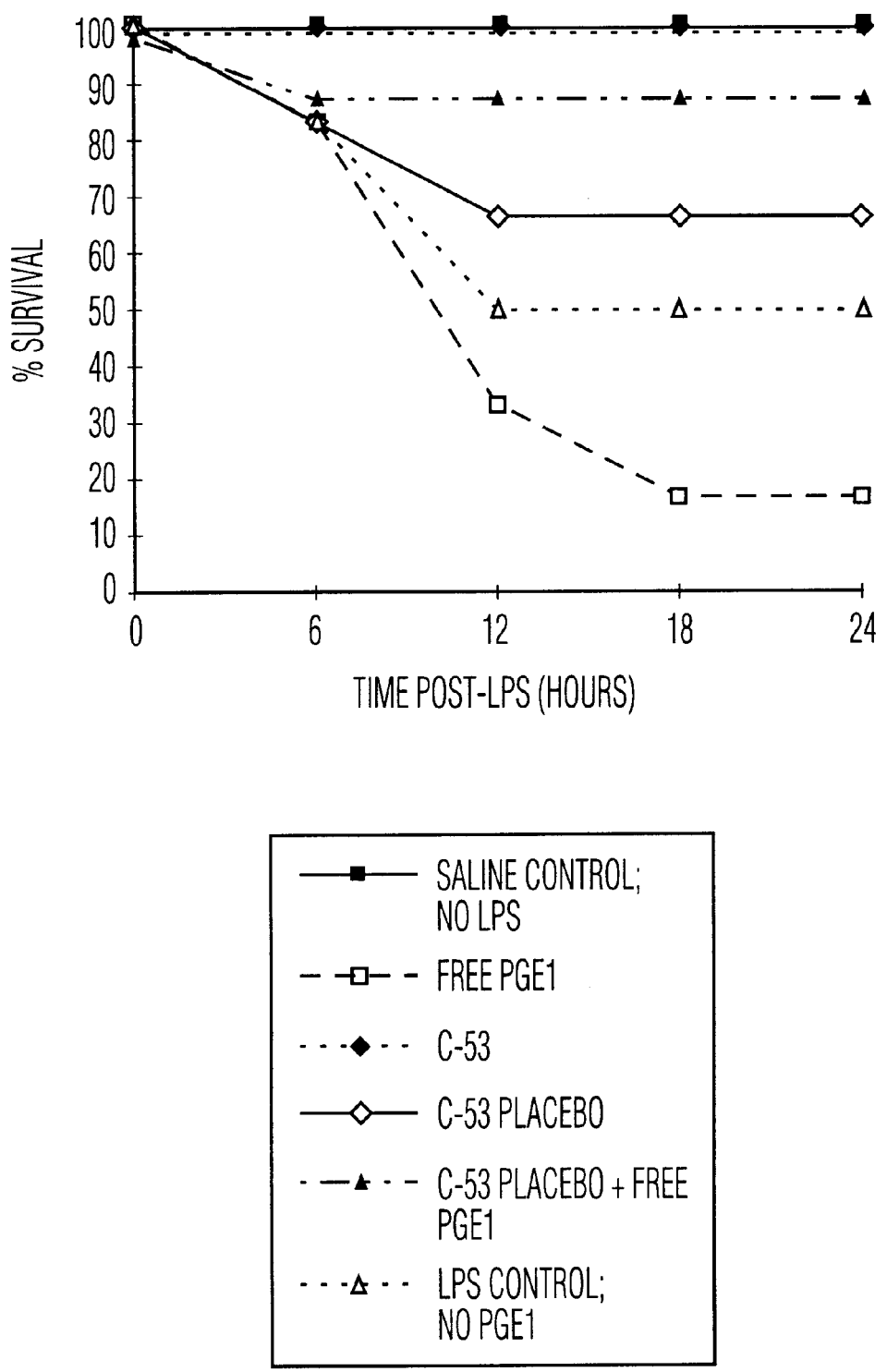
FIG. 10. Placebo Liposomes Attenuate LPS-Induced Mortality and Synergize with Free $PGE_1$ to Increase Survival. X-axis: time (days) post-LPS administration; y-axis: percent survival in treatment group. Filled squares: saline control (no LPS administered); filled diamonds: LUV-$PGE_1$; open diamonds: placebo LUVs plus free $PGE_1$; filled triangle: placebo LUVs; open triangles: LPS control (no liposomes or $PGE_1$); open squares: free $PGE_1$.

Male Sprague-Dawley rats were injected i.v. with 50 g LPS/kg of body weight at time 0. Free $PGE_1$, LUV-$PGE_1$ (40 g/kg $PGE_1$), placebo LUVs (LUVs not containing $PGE_1$; equivalent particle number to the number of liposomes given with the 40 g/kg $PGE_1$—LUV-$PGE_1$ dose) or placebo LUVs (40 g/kg lipid equivalency) plus free $PGE_1$ (40 g/kg). There were 12 rats were in each treatment group. Survival was assessed in each group at 6, 12, 18 and 24 days post-LPS administration. Results are presented in FIG. 10.

Example 7

Rat Endotoxemia/Particle Administration

Figure 11:
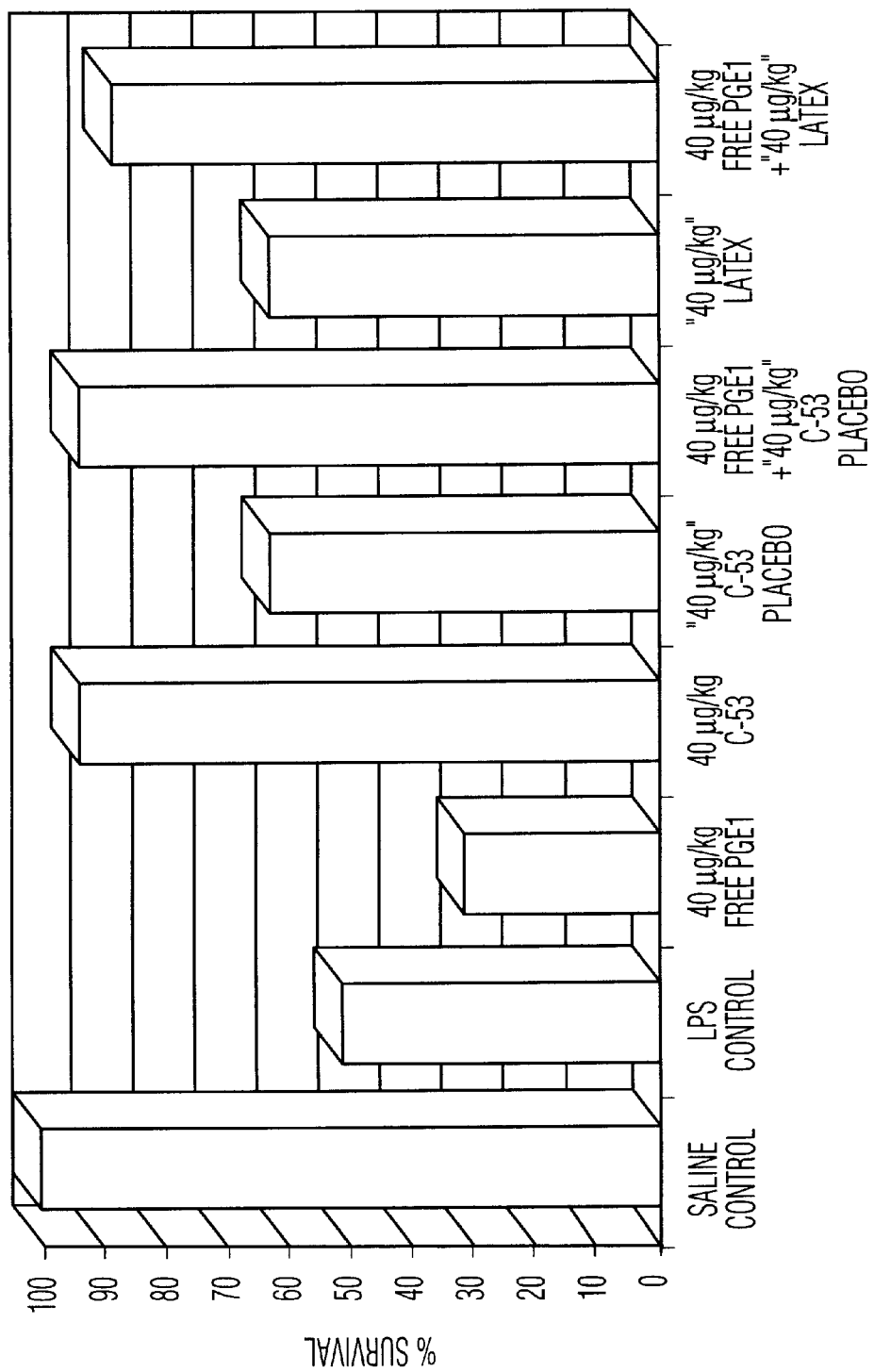
FIG. 11. LUVs and Latex Microspheres Synergize with Free $PGE_1$ to Eliminate Free $PGE_1$-Induced Mortality and to Increase Survival. X-axis: Saline control (no LPS, $PGE_1$ or liposomes), LPS control (LPS, but no liposomes or $PGE_1$), LUV-$PGE_1$, placebo LUVs plus free $PGE_1$, LATEX microspheres plus free $PGE_1$, placebo LUVs, LATEX microspheres; y-axis: percent survival in treatment group.

Male Sprague-Dawley rats were injected i.v. with 50 g/kg LPS at time 0. Free $PGE_1$ (40 g/kg), LUV-$PGE_1$ (40 g/kg $PGE_1$), placebo LUVs (40 g/kg lipid equivalency, i.e., the number of placebo LUVs was equal to the number of LUVs present in connection with a dose of 40 micrograms of prostaglandin E1 per kg of body weight), latex microspheres (the number equivalent to the number of placebo LUVs) or latex microspheres plus free $PGE_1$ (40 g/kg) were simultaneously injected i.v. Survival in each treatment group (16 rats) was assessed at 24 hours. Results are presented in FIG. 11.

Example 8

Rat Endotoxemia Model/Particle Administration

Figure 12:
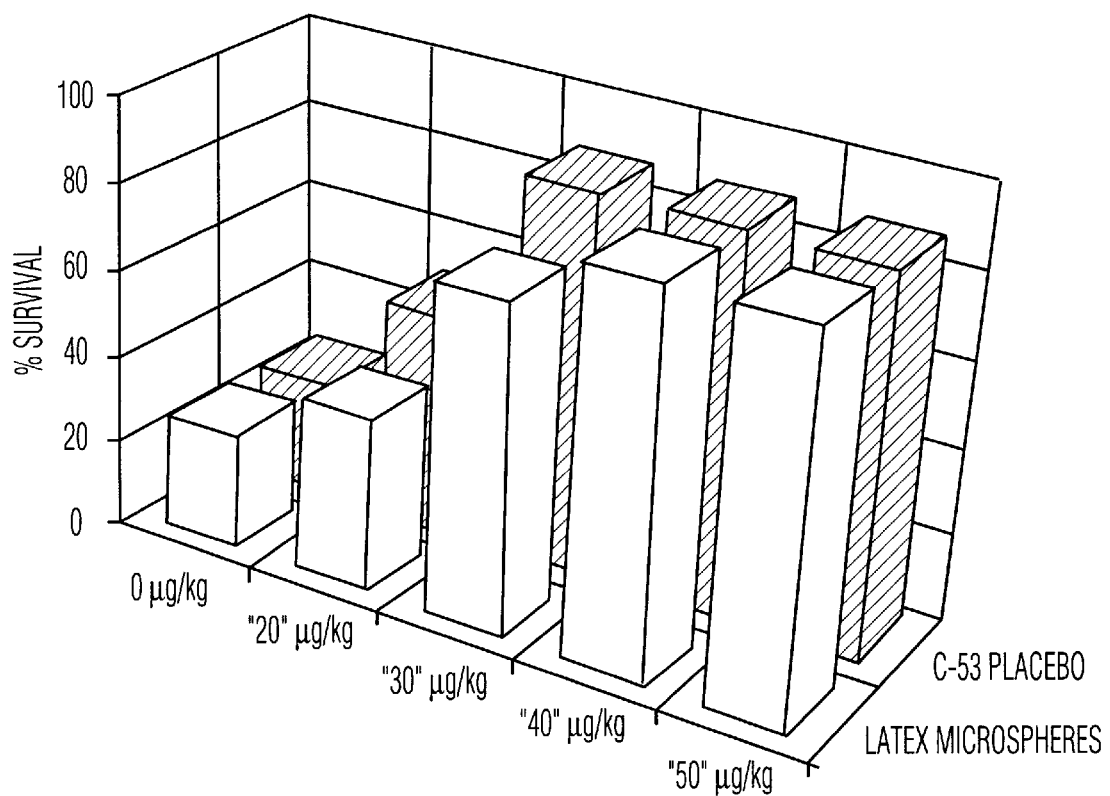
FIG. 12. Increasing the Particle Number Effects an Increased Survival in the Presence of a Constant Dosage of Free $PGE_1$. Saline and LPS controls are not shown. The survival for these groups was 100% and 50%, respectively. X-axis: 0, 20, 30, 40, 50 g/kg; y-axis: percent survival in treatment group; z-axis: no particles administered, LUV-$PGE_1$ administered at a particle equivalency of 40 g/kg plus free $PGE_1$ at the indicated dose.
Figure 13:
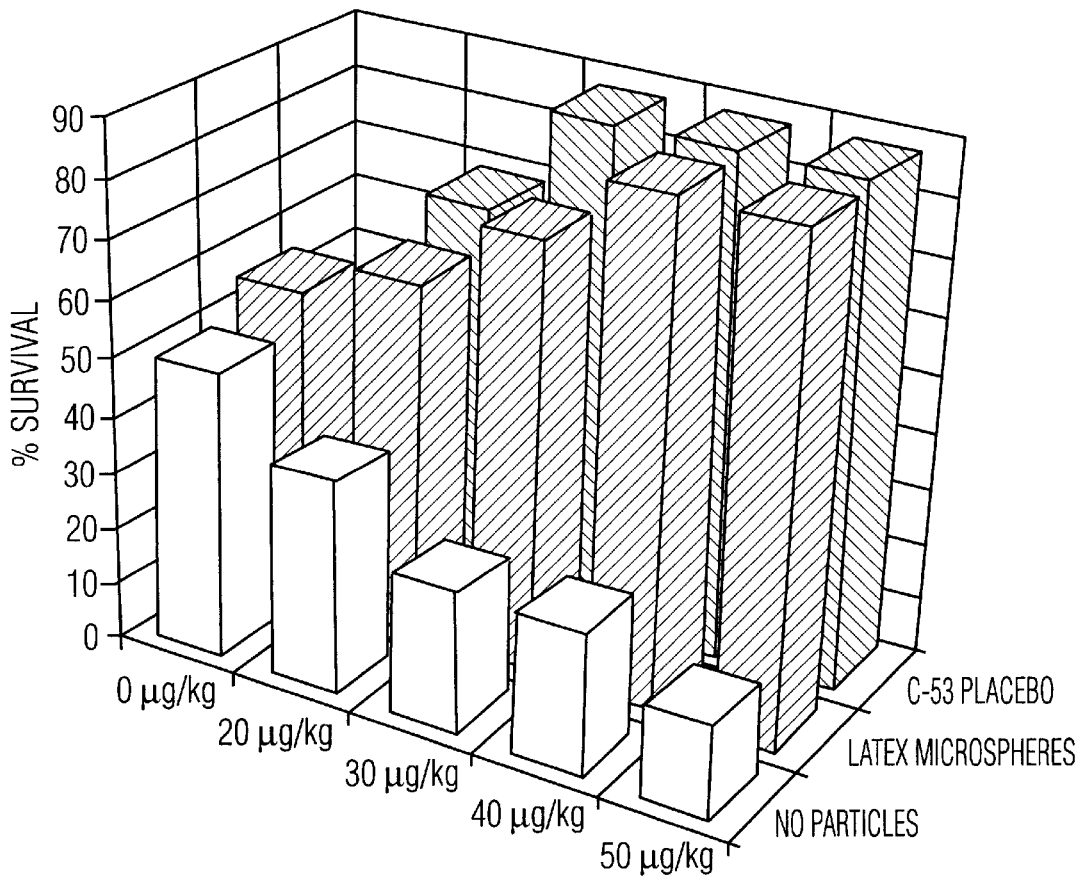
FIG. 13. Increasing the Dosage of Free $PGE_1$ Alone Increases Mortality While Increasing Free $PGE_1$ in the Presence of a Constant Particle Number Increases Survival. Saline and LPS controls are not shown. The survival for these groups was 100% and 50%, respectively. X-axis: 0, 20, 30, 40, 50 g/kg; y-axis: percent survival in treatment group; z-axis: no particles administered, LUV-$PGE_1$ administered at a particle equivalency of 40 g/kg plus free $PGE_1$ at the indicated dose.
Figure 14:
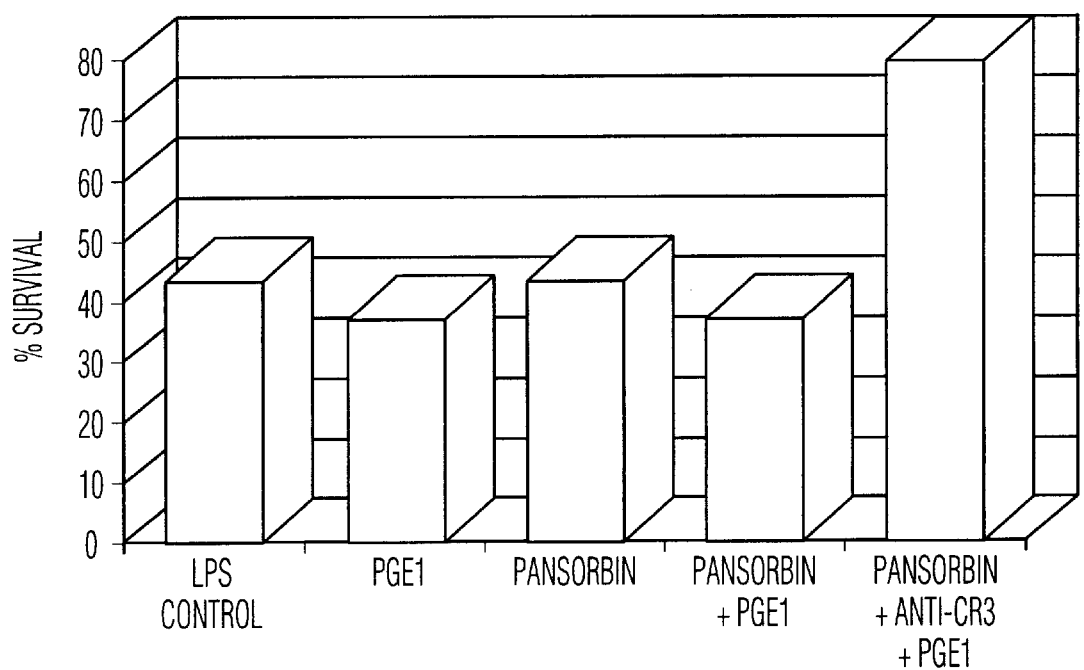
FIG. 14. Leukocyte Phagocytosis of Particles is Obligate for the Protective Effect of Particles and $PGE_1$ During Rat Endotoxemia. X-axis: LPS control; free $PGE_1$; pansorbin; pansorbin plus free $PGE_1$; pansorbin plus free $PGE_1$ plus anti-CR3 monoclonal antibody. Y-axis: percent survival.

Male Sprague-Dawley rats were administered compositions containing $PGE_1$ and a particle, in this case either 100 nm LUVs (LUVs having 100 nm diameters) or 100 nm LATEX microspheres, in which either the $PGE_1$ concentration or particle number was varied while the concentration or number of the other component remained constant. Prostaglandin E1 dose ranged from 25–40 micrograms per kg; the number of particles administered was $1.2-2\times10^{12}$ per kg. The rats were injected i.v. at time 0 with 50 g/kg of LPS. The compositions were administered simultaneously by i.v. injection. Survival in each treatment group (n=16) was assessed at 24 hours. Results of these experiments are presented in FIGS. 12–13.

Example 9

Leukocyte Phagocytosis

Male Sprague-Dawley rats were injected i.v. with 75 mg/kg LPS at time 0. $PGE_1$ (40 g/kg), non-phagocytosable Pansorbin particles ($1.2\times10^{12}$/kg), Pansorbin particles ($1.2\times10^{12}$/kg)+$PGE_1$ (40 g/kg), or Pansorbin particles ($1.2\times10^{12}$/kg) to which anti-CR3 (MoAb OX42) was linked, thus rendering the particle phagocytosable, +$PGE_1$ (40 g/kg) were simultaneously injected i.v. Survival was assessed at 48 hours. Survival in saline controls was 100%. For each treatment group, the number of animals ("n") was 16. Pansorbin™ particles (Calbiochem) are hardened *S. aureus* which have been coated with protein A. They are not phagocytosed by leukocytes in their prepared state, but are phagocytosed when antibody directed to the leukocyte phagocytic receptor CR3 (CD11a/CD18) are coupled to the particles via a protein A-Fc linkage (see Fällman, M., R. Andersson and T. Andersson. 1993. *J. Immunology* 151:330–338, the contents of which are incorporated herein by reference).

What is claimed is:

1. A method of treating a disorder characterized by cell activation/adhesion, inflammation or toxemia, which comprises administering to a subject afflicted with the disorder a composition consisting essentially of:

(a) a pharmaceutically acceptable carrier; and, (b) an anti-disorder effective amount of:

(i) a free prostaglandin; and, (ii) a particle selected from the group consisting of liposomal and latex microsphere particles, wherein the prostaglandin is not entrapped in the particle, wherein less than about half of the prostaglandin is associated with the surface of the particle, and wherein the disorder to be treated is selected from the group consisting of reperfusion injury, restenosis, myocardial infarction, vasculitis, post-traumatic shock, adult respiratory distress syndrome, systemic inflammatory response syndrome, rheumatoid arthritis, systemic lupus erythematosus, juvenile diabetes, multiple sclerosis and Hashimoto's thyroiditis.

2. The method of claim 1, wherein the anti-disorder effective amount comprises from about $10^{-12}$ to about $10^{-3}$ g of the prostaglandin/kg of body weight of the subject.

3. The method of claim 2, wherein the anti-disorder effective amount comprises from about $10^{-8}$ to about $10^{-4}$ g of the prostaglandin/kg body weight.

4. The method of claim 3, wherein the anti-disorder effective amount comprises about $10^{-6}$ g of the prostaglandin/kg body weight.

5. The method of claim 1, wherein the anti-disorder effective amount comprises from about $10^{10}$ to about $10^{14}$ particles per kg of body weight of the subject.

6. The method of claim 5, wherein the particles are approximately spherical and have a diameter of about 100 nm, and wherein the anti-disorder effective amount comprises about $10^{12}$ particles/kg.

7. The method of claim 1, wherein the anti-disorder effective amount comprises from about $10^{-8}$ to about $10^{-4}$ g prostaglandin E1 and from about $10^{10}$ to about $10^{14}$ particles per kg/body weight.

8. The method of claim 1, wherein the disorder to be treated is acute respiratory distress syndrome.

9. The method of claim 1, wherein the particle is a liposome.

10. The method of claim 1, wherein the disorder to be treated is adult respiratory distress syndrome, the anti-disorder effective amount comprises about $10^{-6}$ g of prostaglandin E1 and about $10^{12}$ particles/kg body weight, and wherein the particle is approximately spherical and has a diameter of about 100 nm.

* * * * *

UNITED STATES PATENT AND TRADEMARK OFFICE
CERTIFICATE OF CORRECTION

PATENT NO : 6,030,639
DATED : February 29, 2000
INVENTOR(S) : Janoff, et al.

It is certified that error appears in the above-identified patent and that said Letters Patent are hereby corrected as shown below:

Front Page, Title, Item 54, change "PROSTOGLANDIN" to read --PROSTAGLANDIN --

Front Page, Reference Cited, Item 56, second column under Other Publications, correct "lipo-pgge1, gpe1" to read --lipo-PGE1, PGE1--.

Front Page, Reference Cited, Item 56, second column under Other Publications, correct "J. rheymatol" to read --J. Rheumatol--.

Front Page, under Primary Examiner, correct "Collamudi" to read --Gollamudi--.

Signed and Sealed this

Third Day of April, 2001

Attest:

NICHOLAS P. GODICI

*Attesting Officer*  *Acting Director of the United States Patent and Trademark Office*